United States Patent
Wakabayashi et al.

(10) Patent No.: US 10,708,074 B2
(45) Date of Patent: Jul. 7, 2020

(54) REMOTE MAINTENANCE SYSTEM AND RELAY UNIT

(75) Inventors: Tsutomu Wakabayashi, Tokyo (JP); Shinji Tezuka, Tokyo (JP); Tadashi Nakayama, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 1442 days.

(21) Appl. No.: 13/034,862

(22) Filed: Feb. 25, 2011

(65) Prior Publication Data

US 2011/0205031 A1 Aug. 25, 2011

(30) Foreign Application Priority Data

Feb. 25, 2010 (JP) .................................. 2010-040567

(51) Int. Cl.
| | | |
|---|---|---|
| *G06K 7/01* | (2006.01) | |
| *H04L 12/12* | (2006.01) | |
| *G06F 11/30* | (2006.01) | |
| *G16H 40/40* | (2018.01) | |

(52) U.S. Cl.
CPC .......... *H04L 12/12* (2013.01); *G06F 11/3013* (2013.01); *G06F 11/3055* (2013.01); *G16H 40/40* (2018.01); *Y02D 50/40* (2018.01)

(58) Field of Classification Search
CPC ............ A61N 1/37276; A61N 1/37211; G06F 19/3406; G06F 8/60
USPC ......... 340/10.1, 10.41, 636.1, 636.19, 636.2; 607/5, 32, 60
See application file for complete search history.

(56) References Cited

U.S. PATENT DOCUMENTS

| | | | |
|---|---|---|---|
| 5,339,437 A | | 8/1994 | Yuen |
| 5,417,222 A | * | 5/1995 | Dempsey et al. ............ 600/509 |
| 5,899,855 A | * | 5/1999 | Brown .......................... 600/301 |
| 5,987,519 A | * | 11/1999 | Peifer et al. .................. 709/230 |
| 6,427,088 B1 | * | 7/2002 | Bowman, IV ..... A61N 1/37211 |
| | | | 607/60 |
| 6,480,762 B1 | | 11/2002 | Uchikubo et al. |

(Continued)

FOREIGN PATENT DOCUMENTS

| | | |
|---|---|---|
| CN | 1369818 A | 9/2002 |
| EP | 1850226 A1 | 10/2007 |

(Continued)

OTHER PUBLICATIONS

Search Report dated Jun. 30, 2011 from the European Patent Office in counterpart European application No. 11156016.5.

(Continued)

*Primary Examiner* — Hai Phan
*Assistant Examiner* — Son M Tang
(74) *Attorney, Agent, or Firm* — Sughrue Mion, PLLC

(57) ABSTRACT

A remote maintenance system includes: a medical device which includes: a first power source; a first power source controller which controls an ON/OFF operation of the first power source; a checker which checks a check item; and a first communicator which transmits first information including a result of a check by the checker; and a relay unit which includes: a second power source; a second power source controller which automatically controls an ON/OFF operation of the second power source; and a second communicator which communicates with the first communicator and which receives the first information from the first communicator.

29 Claims, 11 Drawing Sheets

(56) References Cited

U.S. PATENT DOCUMENTS

| | | | |
|---|---|---|---|
| 6,669,196 B1 | 12/2003 | Washko | |
| 6,669,961 B2 | 12/2003 | Kim et al. | |
| 6,727,814 B2* | 4/2004 | Saltzstein et al. | 340/531 |
| 6,804,656 B1* | 10/2004 | Rosenfeld et al. | 705/3 |
| 6,805,667 B2* | 10/2004 | Christopherson et al. | 600/300 |
| 6,832,135 B2* | 12/2004 | Ying | 700/295 |
| 6,993,393 B2* | 1/2006 | Von Arx et al. | 607/60 |
| 7,037,267 B1* | 5/2006 | Lipson et al. | 600/454 |
| 7,038,588 B2* | 5/2006 | Boone et al. | 340/573.1 |
| 7,044,911 B2* | 5/2006 | Drinan et al. | 600/300 |
| 7,072,725 B2* | 7/2006 | Bristol et al. | 700/90 |
| 7,154,398 B2* | 12/2006 | Chen et al. | 340/573.1 |
| 7,181,505 B2* | 2/2007 | Haller et al. | 709/219 |
| 7,827,148 B2* | 11/2010 | Mori et al. | 707/661 |
| 7,860,574 B2* | 12/2010 | Von Arx et al. | 607/60 |
| 7,978,062 B2* | 7/2011 | LaLonde et al. | 340/539.11 |
| RE42,803 E* | 10/2011 | Lipson et al. | 600/454 |
| 8,279,061 B2* | 10/2012 | Soliman | 340/539.12 |
| 2002/0107666 A1 | 8/2002 | Tanaka et al. | |
| 2003/0058097 A1* | 3/2003 | Saltzstein et al. | 340/531 |
| 2003/0233587 A1 | 12/2003 | Sanu | |
| 2004/0015132 A1* | 1/2004 | Brown | 604/131 |
| 2004/0239524 A1* | 12/2004 | Kobayashi | G08C 17/02 340/870.07 |
| 2005/0138470 A1 | 6/2005 | Cromer et al. | |
| 2006/0030891 A1* | 2/2006 | Saltzstein et al. | 607/5 |
| 2006/0142805 A1 | 6/2006 | Katzman et al. | |
| 2007/0255114 A1 | 11/2007 | Ackermann et al. | |
| 2008/0172110 A1* | 7/2008 | Lang | 607/60 |
| 2009/0312821 A1* | 12/2009 | Doerr | A61N 1/37276 607/60 |
| 2010/0014626 A1 | 1/2010 | Fennell et al. | |
| 2010/0222847 A1* | 9/2010 | Goetz | 607/60 |
| 2011/0001605 A1* | 1/2011 | Kiani et al. | 340/5.6 |
| 2011/0060378 A1 | 3/2011 | Tuysserkani | |

FOREIGN PATENT DOCUMENTS

| | | | |
|---|---|---|---|
| JP | 4-101597 A | 4/1992 |
| JP | 10-227400 A | 8/1998 |
| JP | 2001-166958 A | 6/2001 |
| JP | 2002-233504 A | 8/2002 |
| JP | 2003-16213 A | 1/2003 |
| JP | 2006-043270 A | 2/2006 |
| JP | 2006-92035 A | 4/2006 |
| JP | 2007-058442 A | 8/2007 |
| JP | 2007-244804 A | 9/2007 |
| JP | 2008-108111 A | 5/2008 |
| JP | 2008-525084 A | 7/2008 |
| JP | 2013-503722 T | 2/2013 |

OTHER PUBLICATIONS

Extended European Search Report, issued by the European Patent Office in corresponding European Application No. 11156016.5 dated Jan. 24, 2012.

Office Action issued by the Japanese Patent Office dated Apr. 17, 2013 in corresponding Application No. 2010-040567.

Office Action issued by the Japanese Patent Office dated Jul. 4, 2013 in corresponding Application No. 2010-040567.

Communication dated Jun. 24, 2014 from the State Intellectual Property Office of P.R. China in a counterpart application No. 201110044820.7.

Office Action, dated Sep. 20, 2013, issued by the Japanese Patent Office in counterpart Japanese Application No. 2010-040567.

Communication dated Mar. 4, 2015 by the Patent Office of the PR of China in related application No. 201110044820.7.

Office Action dated Dec. 5, 2017 by the European Patent Office in counterpart European Patent Application No. 11156016.5.

* cited by examiner

FIG. 5

| SERIAL NUMBER | DEVICE ID | STATE OF DEVICE | INSTALLA- TION PLACE | NAME OF ADMINIS- TRATOR | MAIL ADDRESS OF ADMINIS- TRATOR | EXPIRATION PERIOD OF POWER SOURCE | EXPIRATION PERIOD OF ELECTRODE PAD | SERIAL NUMBER OF CORRESPONDING RELAY UNIT | ...... |
|---|---|---|---|---|---|---|---|---|---|
| | | | | | | | | | |
| | | | | | | | | | |
| | | | | | | | | | |

FIG. 6

| SERIAL NUMBER | UNIT ID | STATE OF UNIT | INSTALLA- TION PLACE | NAME OF ADMINIS- TRATOR | MAIL ADDRESS OF ADMIN- ISTRATOR | EXPIRATION PERIOD OF POWER SOURCE | SERIAL NUMBER OF CORRE- SPONDING MEDICAL DEVICE | MAIL TRANSMIS- SION STANDARD | WAITING TIME PERIOD TW | ...... |
|---|---|---|---|---|---|---|---|---|---|---|
| | | | | | | | | | | |
| | | | | | | | | | | |
| | | | | | | | | | | |

FIG. 7

| | |
|---|---|
| I { | SUBJECT : [NK KOHDEN] MESSAGE ABOUT MAINTENANCE OF AED |
| T { | APRIL 1, 2010, 12:00 |
| C { | IN AED, "EXPIRATION PERIOD OF PADS HAS ELAPSED" WAS DETECTED. |
| A { | INSTALLATION PLACE "SOUTH TICKET GATE" |
| N { | SERIAL NO. "012345" |
| M { | CHECK STATUS OF AED, AND CONTACT AT 03-5996-XXXX. |

REMOTE MAINTENANCE SYSTEM AND RELAY UNIT

BACKGROUND OF THE INVENTION

The present invention relates to a remote maintenance system which checks and manages states of various medical devices, and also to a relay unit which is to be used in such a remote maintenance system.

As a related-art apparatus of this kind, there is an apparatus which detects extraction or abnormal state of an emergency device disposed in a case, and which notifies a managing device (see JP-A-2007-58442, JP-A-2007-244804 and JP-A-2006-043270). In such an apparatus, it is necessary to monitor whether the emergency device is extracted, and hence constant monitoring is required. This necessitates a power supply such as a commercial power supply. Therefore, the installation place is limited, and such an apparatus cannot be used anywhere. It may be contemplated that such an apparatus is configured so as to use a large battery in place of a commercial power supply. In this case, however, a countermeasure against battery rundown is required, and therefore such an apparatus is inadequate in a long-term use. In the case where such an apparatus is installed in a remote place, battery replacement cannot be frequently performed. Consequently, there remain problems to be solved.

In the case of an apparatus in which a medical device can be housed, the size of the apparatus is large. In the case where the size of a medical device itself is large, the apparatus cannot house the medical device.

Also, there is a related-art apparatus in which an AED incorporates a receiver, and alert information such as maintenance is sent from the outside to the receiver to inform the user of the AED of an alert status (see the description of FIG. 5 in JP-T-2008-525084). In the apparatus, the necessity of maintenance or the like can be informed to the user of the AED. However, a professional company which manages the AED cannot use the apparatus in maintenance of the AED. When, for example, the AED itself breaks down, moreover, alert information cannot be sent and cannot be informed. Furthermore, there is a possibility that, when the AED performs a process such as reception of information, the user must wait to use the AED.

Furthermore, there is a system of performing maintenance in which a processor monitors medical devices in hospitals through a LAN, and a computer in a service center is connected to the hospitals through a network (see JP-A-2002-233504). The system is large in scale, and functions on the premise that it is used in an environment where the power such as commercial AC power is always supplied, because the monitoring of the medical devices is naturally always performed. Therefore, the system cannot be used in an environment where the installation place of a medical device is not considered.

SUMMARY

It is therefore an object of the invention to provide a remote maintenance system which can be used in an environment where the installation place of a medical device is not considered, and in which a certain amount of long-term operation is particularly ensured even when commercial power is not supplied.

It is also an object of the invention to provide a relay unit which can be used in such a remote maintenance system.

In order to achieve the object, according to the invention, there is provided a remote maintenance system comprising: a medical device which includes: a first power source; a first power source controller which controls an ON/OFF operation of the first power source; a checker which checks a check item; and a first communicator which transmits first information including a result of a check by the checker; and a relay unit which includes: a second power source; a second power source controller which automatically controls an ON/OFF operation of the second power source; and a second communicator which communicates with the first communicator and which receives the first information from the first communicator.

The relay unit may include a third communicator which communicates with a fourth communicator included in a maintenance center device, and the third communicator may transmit, to the fourth communicator, second information including the result of the check.

The maintenance center device may include a fifth communicator which communicates with an administrator, and the fifth communicator may transmit, to the administrator, a notification based on the second information transmitted from the third communicator.

The second power source controller may automatically turn ON the second power source, at prescribed intervals or at a prescribed time, and the second power source controller may automatically turn OFF the second power source, after the second communicator receives the first information including the result of the check from the first communicator of the medical device, and then the third communicator transmits the second information including the result of the check to the fourth communicator of the maintenance center device.

The first power source controller may turn ON the first power source, at prescribed intervals or at a prescribed time, and the first power source controller may turn OFF the first power source, after the first communicator transmits the first information including the result of the check to the second communicator of the relay unit.

The second power source controller may turn ON the second power source before the first power source controller turns ON the first power source.

One of the medical device, the relay unit and the maintenance center device may include a determiner which determines whether the check item is normal or abnormal based on the result of the check.

When the determiner determines that the check item is abnormal, a fifth communicator of the maintenance center device may transmit a notification to an administrator.

The maintenance center device may change and update setting information of the relay unit and the medical device, through the first to fourth communicators.

The check item may include at least one of a remaining amount of electric power of the first power source and an expiration period of an accessory of the medical device.

Operation of at least one of the medical device, the relay unit, the maintenance center device and a notification to an administrator check, which is requested by a user, may be checked.

The first information transmitted from the first communicator of the medical device may include information for identifying the medical device and information related to an installation place of the medical device.

The check item may include communication between the medical device and the relay unit, and when the communication is disabled, the determiner may determine that the communication is abnormal.

The second information transmitted from the third communicator of the relay unit to the fourth communicator of the maintenance center device may include information related to the relay unit.

When communication between the first communicator and the second communicator is established, the medical device and the relay unit may be synchronized in time with each other.

The second power source controller may turn ON the second power source, after elapse of a prescribed time period from a timing when communication between the first communicator and the second communicator is established.

After communication between the first communicator and the second communicator is established, the medical device and the relay unit may be synchronized in time with each other.

The first power source controller may control the ON/OFF operation of the first power source by an automatic operation or an external operation.

The medical device may be an AED.

The first power source and the second power source may be identical with each other.

At least one of the first power source and the second power source may be a battery.

Communication between the first communicator and the second communicator may be short-range wireless communication.

After elapse of a prescribed time period, the third communicator of the relay unit may transmit the second information to the fourth communicator of the maintenance center device.

In order to achieve the object, according to the invention, there is also provided a relay unit which is to be used in a remote maintenance system which includes a medical device, which transmits first information based on self-checking, the relay unit and a maintenance center device, the relay unit comprising: a battery; a battery controller which turns ON/OFF the battery at prescribed intervals or at a prescribed time; a wireless communicator which performs short-range wireless communication with the medical device; and a communicator which transmits second information corresponding to the first information, which is transmitted from the medical device and is acquired from the wireless communicator, to the maintenance center device.

BRIEF DESCRIPTION OF THE DRAWINGS

FIG. 5 is a view showing an example of contents of a memory table disposed in the embodiment of the remote maintenance system of the invention.

FIG. 6 is a view showing an example of contents of the memory table disposed in the embodiment of the remote maintenance system of the invention.

FIG. 7 is a view showing an example of contents of an electronic mail sent from the maintenance center device included in the remote maintenance system of the invention.

DETAILED DESCRIPTION OF EMBODIMENTS

Figure 1:
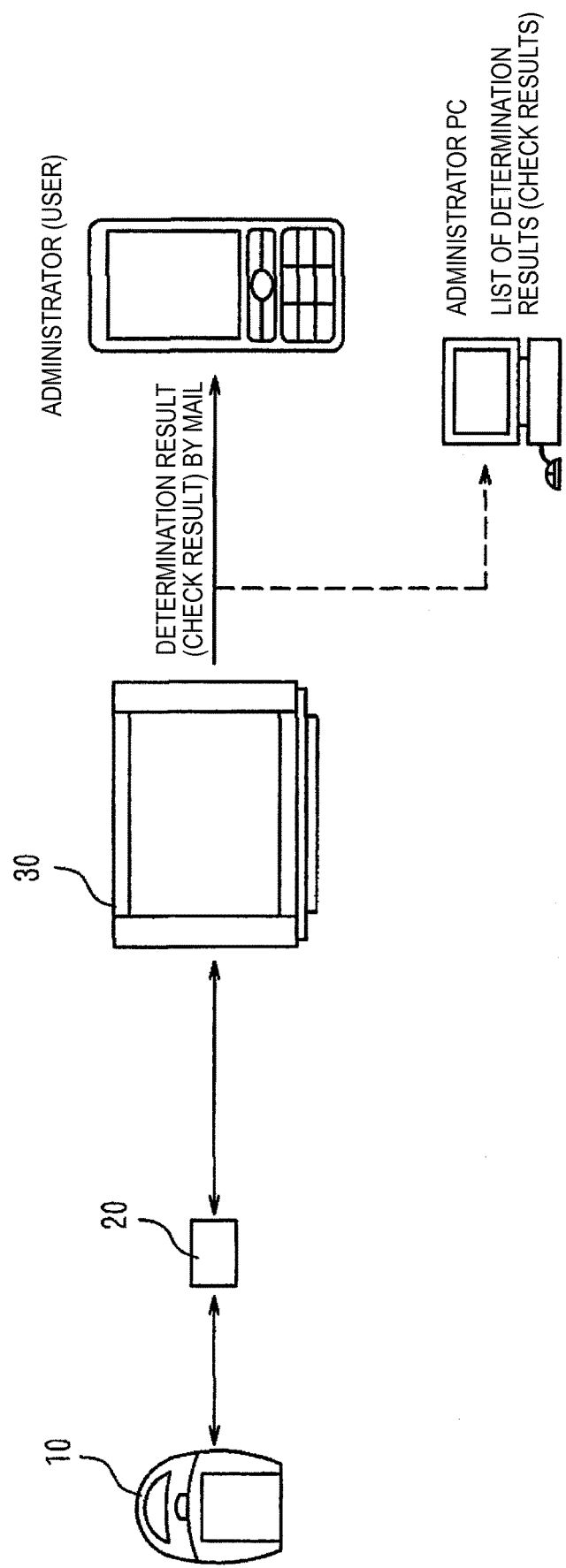
FIG. 1 is a diagram of an embodiment of the remote maintenance system of the invention.

Hereinafter, embodiments of a remote maintenance system and a relay unit of the invention will be described with reference to the accompanying drawings. In the figures, the identical components are denoted by the same reference numerals, and duplicated description will be omitted. FIG. 1 is a diagram of the embodiment of the remote maintenance system of the invention. The remote maintenance system includes a medical device 10, a relay unit 20, and a maintenance center device 30. Usually, the medical device 10 and the relay unit 20 are used in a plural number. Basically, the medical device 10 corresponds to the relay unit 20 in a one-to-one relationship. Alternatively, the relay unit 20 may have a configuration to correspond to a plurality of medical devices 10.

Figure 2:
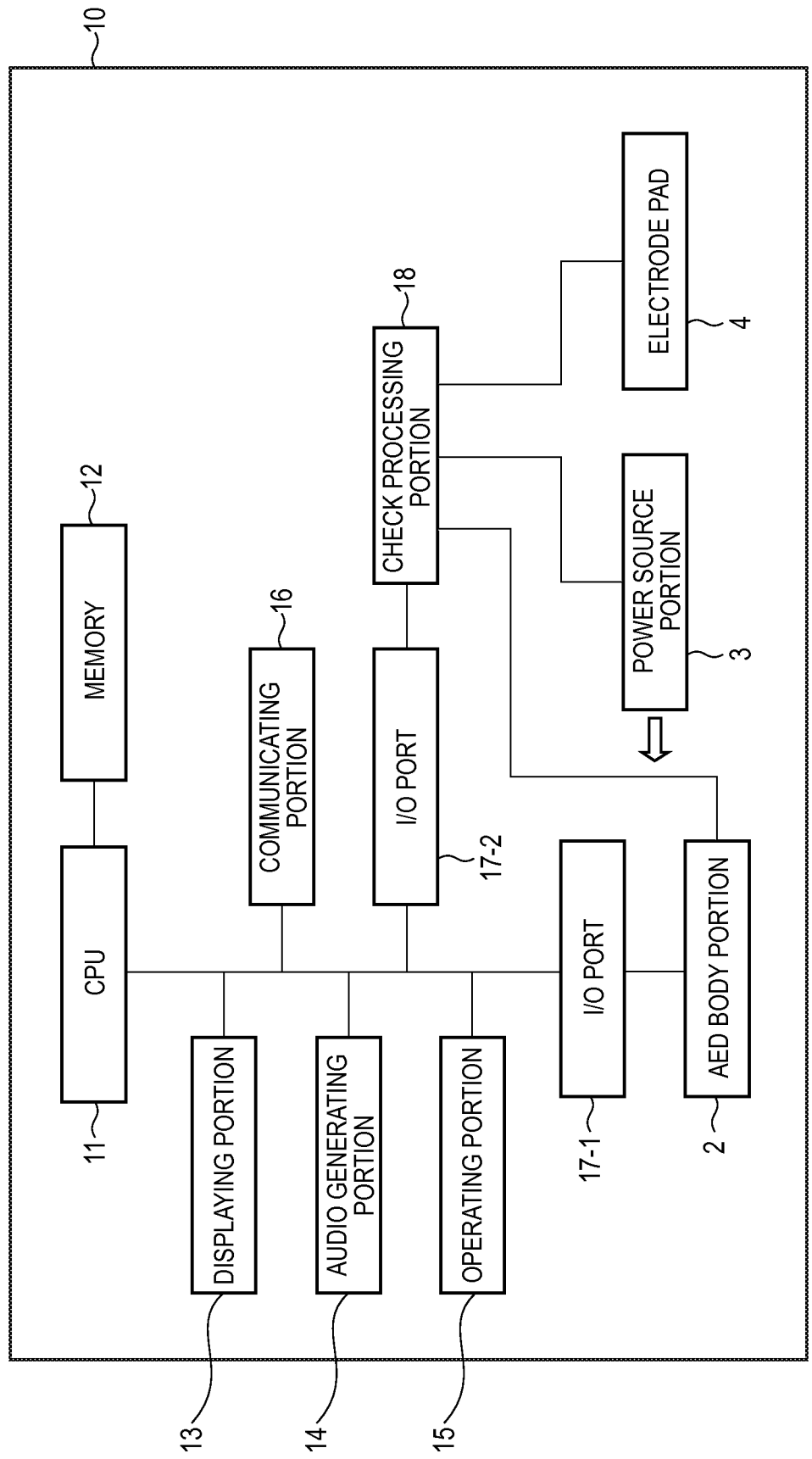
FIG. 2 is a block diagram showing an embodiment of a medical device included in the remote maintenance system of the invention.

As the medical device 10 in the embodiment, an AED (Automatic External Defibrillator) having the configuration shown in FIG. 2 is exemplified. The medical device 10 includes a CPU 11 which controls various portions, and a memory 12 is connected to the CPU 11. The memory 12 stores programs which are executed in the case where the medical device functions as an AED, those for automatic checking, identification information (the manufacturer's serial number, the device ID, etc.) for identifying the medical device, information related to the installation place, and the like. The memory 12 is used also as a working memory.

Furthermore, a displaying portion 13, an audio generating portion 14 such as a speaker, an operating portion 15 including various switches, a communicating portion 16, which is a first communicator, and I/O ports 17-1, 17-2 are connected to the CPU 11. An AED body portion 2 is connected to the I/O port 17-1, and a check processing portion 18 is connected to the I/O port 17-2.

The check processing portion 18 is connected to the AED body portion 2, a power source portion 3 configured by a battery, and electrode pads 4, and checks the states of the components. For example, the check processing portion 18 performs: on the AED body portion 2, checking processes such as whether the circuit function of the portion adequately operates or not; on the power source portion 3, checking processes such as whether the output is adequate or not, and detection of the remaining amount of battery power; and, on the electrode pads 4 which are accessories, checking processes such as whether an adequate impedance is maintained, and whether the expiration period has elapsed or not.

The power source portion 3, which is a first power source, is usually in a turned-OFF state, and, when a lid of a case of the AED is opened, performs power-ON to supply power to various portions. Even in the turned-OFF state, the CPU 11 receives a power supply in the sleep mode, and, at a predetermined time (for example, a predetermined time once a day) based on a timer which is incorporated in the CPU, controls the power source so as to be turned ON to supply power to the communicating portion 16, the I/O port 17-2, and the check processing portion 18. In this way, the CPU 11 functions as a first power source controller. Namely, the term of power-ON means the power source control of transferring from the sleep state to the operation state. In the medical device, the power ON/OFF control may be automatically performed, or in response to an external operation which is conducted by the user or the like.

At the predetermined time, the CPU 11 controls the check processing portion 18 so as to check the states of the AED body portion 2, power source portion 3 and electrode pads 4, which are to-be-checked components, and obtains a result of the check. Information related to the check result is transmitted from the communicating portion 16, as it is or after being processed into transmission information in which predetermined information such as identification information (the manufacturer's serial number, the lot number, the product type, etc.) for identifying the medical device, information related to the installation place of the medical device, and the like is added to the check result information.

The to-be-checked components are not limited to the above-mentioned components, and, in the case where the invention is applied to a medical device other than an AED, may include to-be-checked components corresponding to the medical device. In the case of a medical device which uses a reagent, for example, information related to the remaining amount of the reagent and the like may be included.

The process, which is applied to the information related to the check result, means that the CPU 11 functions as a determiner, determination of normality/abnormality is performed based on, for example, the remaining amount of battery power in the power source portion 3, and then a result of the determination is transmitted. If the determination result indicates abnormality, the CPU 11 causes, for example, an LED of the displaying portion 13 to be lit, thereby indicating abnormality of the medical device 10. Each of the power source portion 3 and the electrode pads 4 has an expiration period. Information of the expiration periods may be stored in the memory 12, or held by the to-be-checked components such as the power source portion 3 and the electrode pads 4. In the checking process, the CPU 11 compares the time of the timer which is incorporated in the CPU, with the expiration period information. If the expiration period has elapsed, the elapse of the expiration period is transmitted in the form of information from the communicating portion 16, and an LED of the displaying portion 13 is lit to indicate the elapse of the expiration period.

Figure 3:
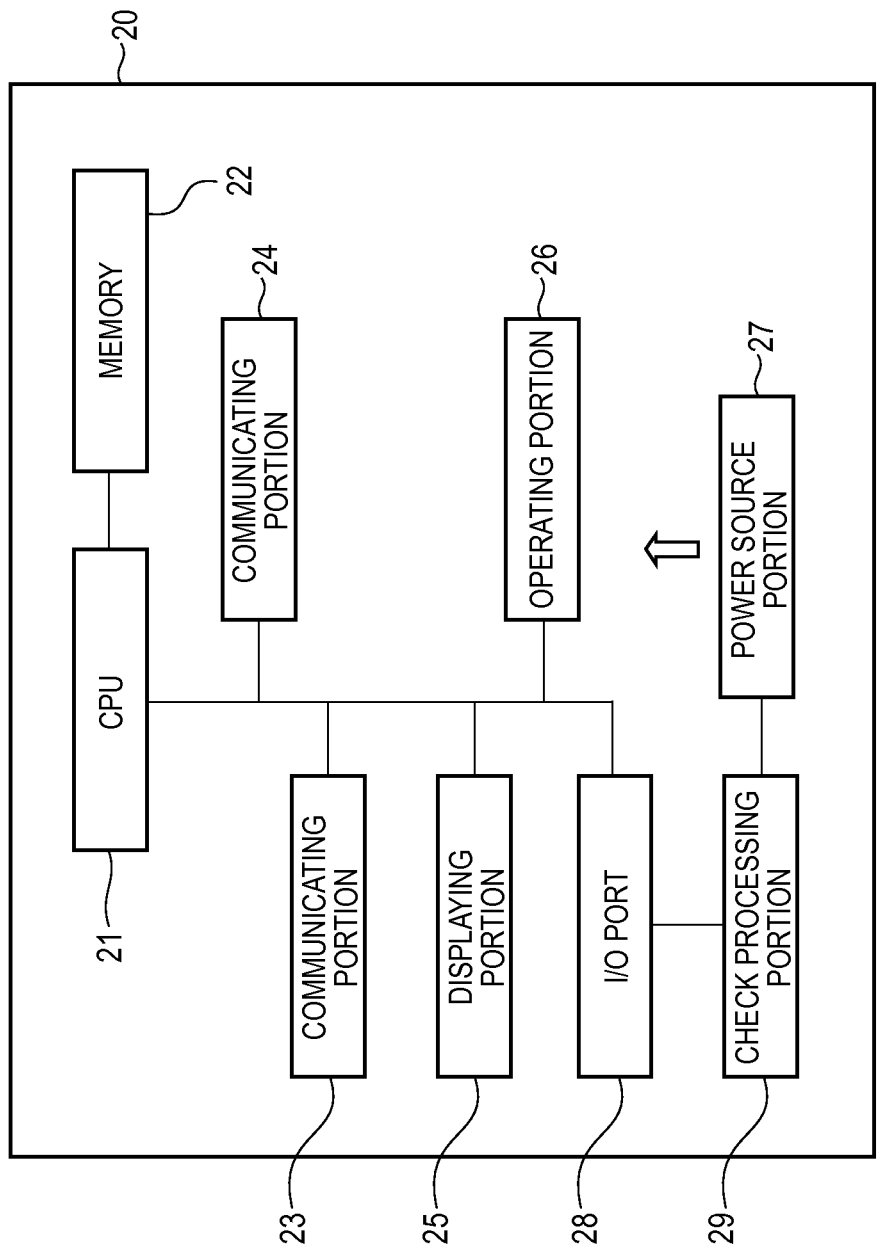
FIG. 3 is a block diagram showing an embodiment of a relay unit included in the remote maintenance system of the invention.

As shown in FIG. 3, the relay unit 20 includes a CPU 21, and a memory 22 is connected to the CPU 21. The memory 22 stores programs which are used by the CPU 21, identification information (the manufacturer's serial number, the lot number, the product type, etc.) for identifying the relay unit, information related to the installation place of the relay unit, and the like. The memory 22 is used also as a working memory.

Furthermore, a communicating portion 23, which is a second communicator, a communicating portion 24, which is a third communicator, a displaying portion 25, and an operating portion 26 are connected to the CPU 21 of the relay unit 20. The communicating portions 23, 24 constitute a communicating unit. The communicating portion 23 has a configuration for communicating with the communicating portion 16 of the medical device 10. The communication between the communicating portions 23 and 16 is performed by, for example, a digital wireless communication system based on Bluetooth. The communicating portions 23 and 16 are requested to be placed with being separated by a short distance, and may be connected to each other by wireless communication such as infrared communication, or wire-connected to each other.

The relay unit 20 includes a power source portion 27, which is a second power source, and which is configured by a battery. The power source portion 27 supplies electric power to various portions. In the case where setting such as initialization is to be performed by an operation through the operating portion 26, for example, a mode where the power source portion 27 supplies electric power to various portions is set. When the mode is returned to the normal mode by an operation through the operating portion 26, a power supply in which the CPU 21 is set to the sleep mode is performed. In the sleep mode, the CPU 21 controls the power source portion 27 so as to turn ON the power supply at a predetermined time (for example, a predetermined time once a day, and at the same time as that in the medical device 10) based on a timer which is incorporated in the CPU, to supply electric power to various portions. As described above, the CPU 21 functions as a second power source controller. In the above, the power source portion 3, which is the first power source, and the power source portion 27, which is the second power source, are separately configured. In the case where, for example, the medical device and the relay unit are disposed in very close proximity to each other, or substantially integrated with each other, the first and second power sources may be configured as the same power source. Although the relay unit transmits information to the maintenance center device, the entire information or predetermined information may be directly transmitted to the user.

A check processing portion 29 is connected to the CPU 21 through an I/O port 28. The check processing portion 29 detects the remaining amount of battery power in the power source portion 27, and notifies the CPU 21 of the detected remaining amount. The check processing portion 29 may perform also detection other than that of the remaining amount of battery power in the power source portion 27, and, for example, may detect the state of the communicating portion 23 and notify the CPU 21 of the detected state.

At the predetermined time, the CPU 21 controls the check processing portion 29 so as to check the states of the power source portion 27 and other portions, which are to-be-checked components, and obtains a result of the check. Information related to the check result is transmitted from the communicating portion 24, as it is or after being processed into transmission information in which predetermined information such as identification information (the manufacturer's serial number, the lot number, the product type, etc.) for identifying the relay unit, information related to the installation place of the relay unit, and the like, is added to the check result information.

When the CPU 21 turns ON the power supply from the power source portion 27, the CPU receives information based on the check result from the medical device 10 through the communicating portion 23, transmits information based on the received information to the maintenance center device 30 through the communicating portion 24, and then turns OFF the power source portion 27. Also in this case, the CPU 21 transmits the information received from the medical device 10 as it is or after being processed. The process means, for example, that the CPU 21 functions as a determiner, determination of normality/abnormality is performed, and then a result of the determination is transmitted.

In the transmission, the information based on the result of the check by the above-described check processing portion 29 is transmitted together with the information received from the medical device 10. Furthermore, predetermined information such as identification information (the manufacturer's serial number, the lot number, the product type, etc.) for identifying the relay unit 20 is added to the information, and then the transmission is performed.

Figure 4:
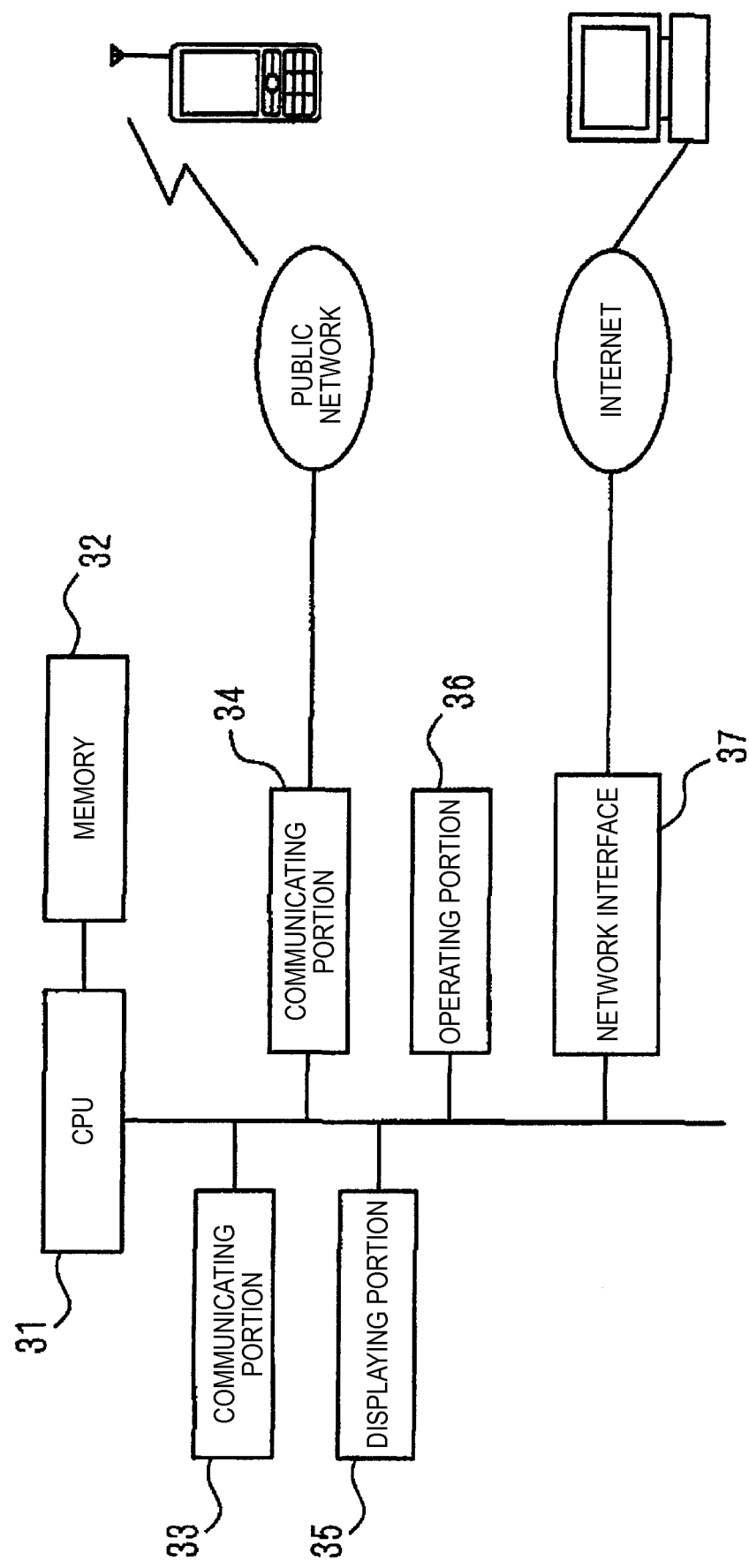
FIG. 4 is a block diagram showing an embodiment of a maintenance center device included in the remote maintenance system of the invention.

As shown in FIG. 4, the maintenance center device 30 includes a CPU 31 which generally controls the device. A memory 32 is connected to the CPU 31. In the memory 32, stored are a medical device table which is shown in FIG. 5, and which stores maintenance information related to all medical devices to be maintained, and a relay unit table which is shown in FIG. 6, and which stores maintenance information of relay units disposed correspondingly to the all medical devices. The memory 32 is used also as a working memory.

A communicating portion 33, which is a fourth communicator, a communicating portion 34, which is a fifth communicator, a displaying portion 35, an operating portion 36, and a network interface 37 are connected to the CPU 31. The communicating portion 33 is used for communicating with the communicating portion 24 of the relay unit 20, and connected to, for example, a wired or wireless public network. The communicating portions 33, 34 function as an interface through which the CPUs 31, 21 transmit and receive an electronic mail by means of electronic mail communication software. Similarly, also the communicating portion 34 is connected to the public network, and functions as an interface through which the CPU 31 transmits and receives an electronic mail to a portable telephone or the like by means of electronic mail communication software.

The Internet is connected to the network interface 37, and the CPU 31 performs a process as a database server, thereby enabling an external person to access and refer to information through a personal computer or the like. A power source portion is disposed also in the maintenance center device 30, processes electric power from a commercial power supply, and supplies the processed electric power to various portions. The power source portion is not shown in the figures.

The CPU 31 receives information based on the check result from the communicating portion 33, forms the result into, for example, a list, and holds the list in the database of the memory 32. The database is configured by the medical device table shown in FIG. 5, and the relay unit table shown in FIG. 6. In the medical device table, the manufacturer's serial number, the state of the device, the installation place, the name of the administrator, the mail address of the administrator, the expiration period of the power source, the expiration period of the electrode pads, the manufacturer's serial number of the corresponding relay unit, and the like are correspondingly stored. In the relay unit table, the manufacturer's serial number, the state of the unit, the installation place, the name of the administrator, the mail address of the administrator, the expiration period of the power source, the manufacturer's serial number of the corresponding medical device, the mail transmission standard, the waiting time period TW (the transmission waiting time period TW of information based on the check result), and the like are correspondingly stored. As described above, the information of the databases can be externally accessed and referred through the personal computer or the like.

The CPU 31 functions as a determiner to determine normality/abnormality by using the check result, and, if abnormality is detected, or if the sent information includes a determination result indicative of abnormality, determines whether notification to the administrator is necessary or not. If, as a result of the determination, it is determined that notification is necessary, the CPU produces a message to be transmitted, fetches the destination address of the message from the database of the memory 32, and transmits the message in the form of an electronic mail to the portable telephone or the like through the communicating portion 34. The transmitted electronic mail has contents such as shown in FIG. 7. For example, it is assumed that the mail includes Subject I, Date and time T, Contents C, Installation place A, Manufacturer's serial number N, and Message of correspondent contents M.

Figure 8:
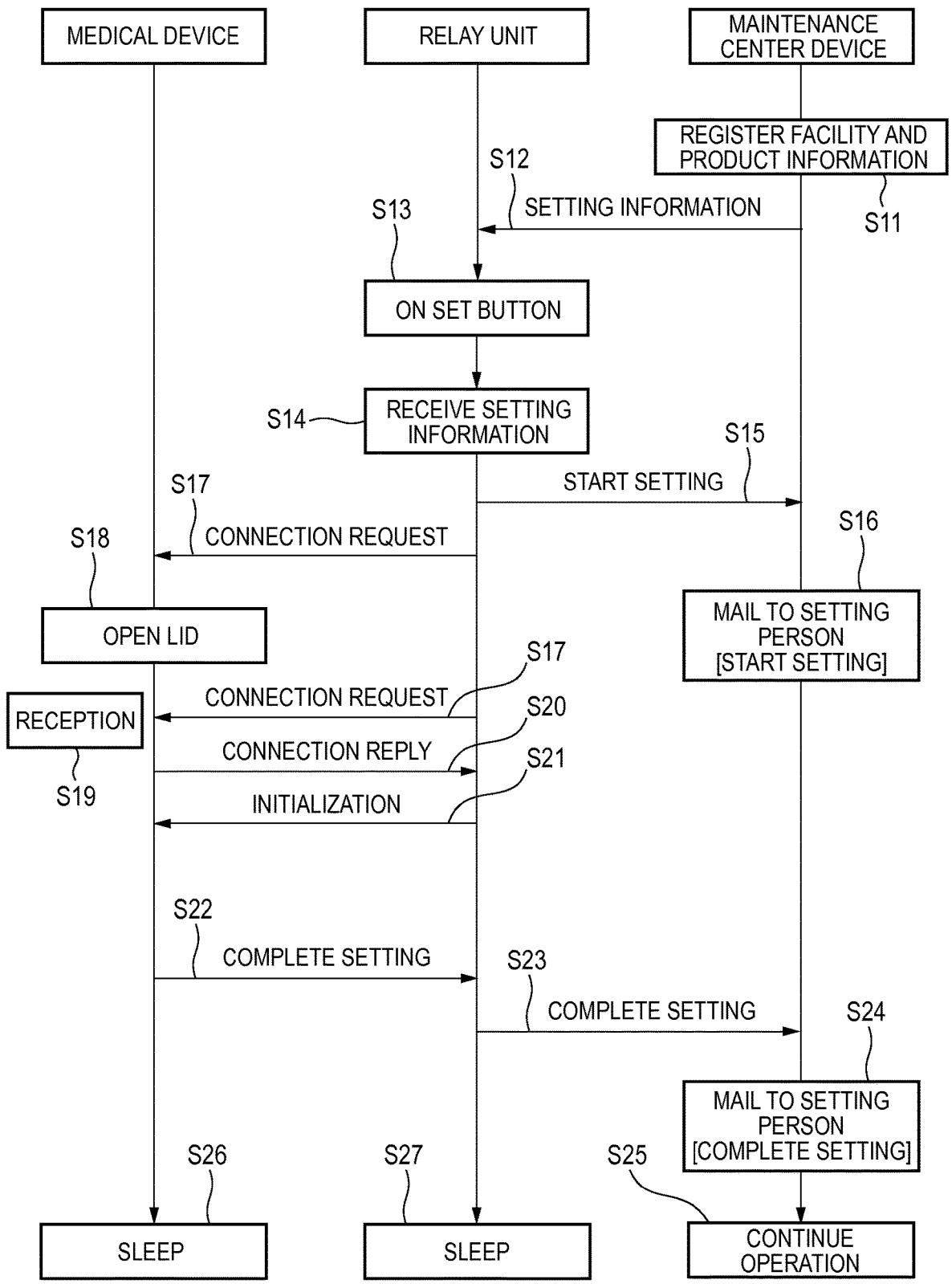
FIG. 8 is a sequence diagram showing an initial setting process in the embodiment of the remote maintenance system of the invention.

In the thus configured remote maintenance system, in initialization or subsequent updation, setting can be performed by mutual communication. FIG. 8 shows the sequence in this case. At first, the facility and product information are registered to construct the above-described database (S11). For each set of a medical device and a relay unit corresponding to the medical device, for example, the data and time when setting is to be performed is written in an activation program for a setting program. The setting program is activated at the preset date and time. The setting information is fetched from the corresponding information column of the database, and assembled into a mail to be transmitted, the mail address of the relay unit 20 of the destination is read out, and the electronic mail of the setting information is transmitted from the communicating portion 33 to the relay unit 20 (S12).

At the preset date and time, the setting person (administrator) who has performed the setting goes to the place where the relay unit 20 is disposed, and, at about a timing when the electronic mail of the setting information is transmitted, operates a set button which is disposed in the operating portion 26 of the relay unit 20 (S13). This causes the CPU 21 to receive the electronic mail of the setting information (S14), and transmit an electronic mail of start of setting to the maintenance center device 30 through the communicating portion 24 (S15). In the relay unit 20, as a result, setting information which is required by the relay unit 20 (the mail address of the maintenance center device 30, the transmission waiting time period TW of information based on the check result, and the like) is stored in the memory 22. Furthermore, time information is sent as the setting information, and hence the CPU 21 sets the time of the own timer, and causes the operation to be started.

On the other hand, the maintenance center device 30 receives the setting start mail indicated in step S15, and transmits an electronic mail informing of setting start, to a portable telephone of the setting person (administrator) through the communicating portion 34 (S16).

Furthermore, the CPU 21 of the relay unit 20 controls the communicating portion 23 so as to transmit a connection request command in order to establish a communication link with the medical device 10 (S17). Here, the setting person already receives the electronic mail which is transmitted in step S16, and which informs of setting start. Therefore, the setting person goes to the place in which the medical device 10 is disposed, and which is near the installation place of the relay unit 20, and then opens the lid of the medical device 10 to activate the medical device 10 (S18).

The CPU 11 of the medical device 10 receives a transmission request command which is sent from the relay unit 20, through the communicating portion 16 (S19), and transmits a connection reply command through the communicating portion 16 (S20). In this way, the communication link between the medical device 10 and the relay unit 20 is established. When the communication link is established, the CPU 21 of the relay unit 20 transmits setting information (the manufacturer's serial number, the device ID, time information, and the like) which is directed to the medical device 10, through the communicating portion 23 (S21).

The setting information which is transmitted in step S21 from the relay unit 20 is received by the CPU 11 through the communicating portion 16, and then basically stored in the memory 12, thereby completing the setting process. The time information is input to the CPU 11, and the CPU sets the time of the own timer and starts the operation of the timer. Then, the CPU 11 prepares a setting complete command, and transmits the command to the relay unit 20 through the communicating portion 16 (S22).

The setting complete command is received by the CPU 21 through the communicating portion 23. The CPU 21 prepares an electronic mail which is directed to the maintenance center device 30, and which indicates the setting completion, and transmits the mail with using the mail address of the maintenance center device 30 which is stored as the setting information in the memory 22 (S23). The CPU 31 of the maintenance center device 30 which receives the electronic mail indicative of the setting completion transmits an electronic mail indicative of the setting completion to the portable telephone of the setting person through the communicating portion 34 (S24), and continues necessary operations (S25).

Upon receiving the electronic mail indicative of the setting completion, the setting person closes the lid of the medical device 10 to set the medical device 10 to the sleep mode (S26), and, after the relay unit 20 transmits the electronic mail indicative of the setting completion, also the relay unit 20 is set to the sleep mode (S27). The initial setting process is performed as described above. Also in updation or the like, a setting process similar to the above-described initial setting process may be performed.

Figure 9:
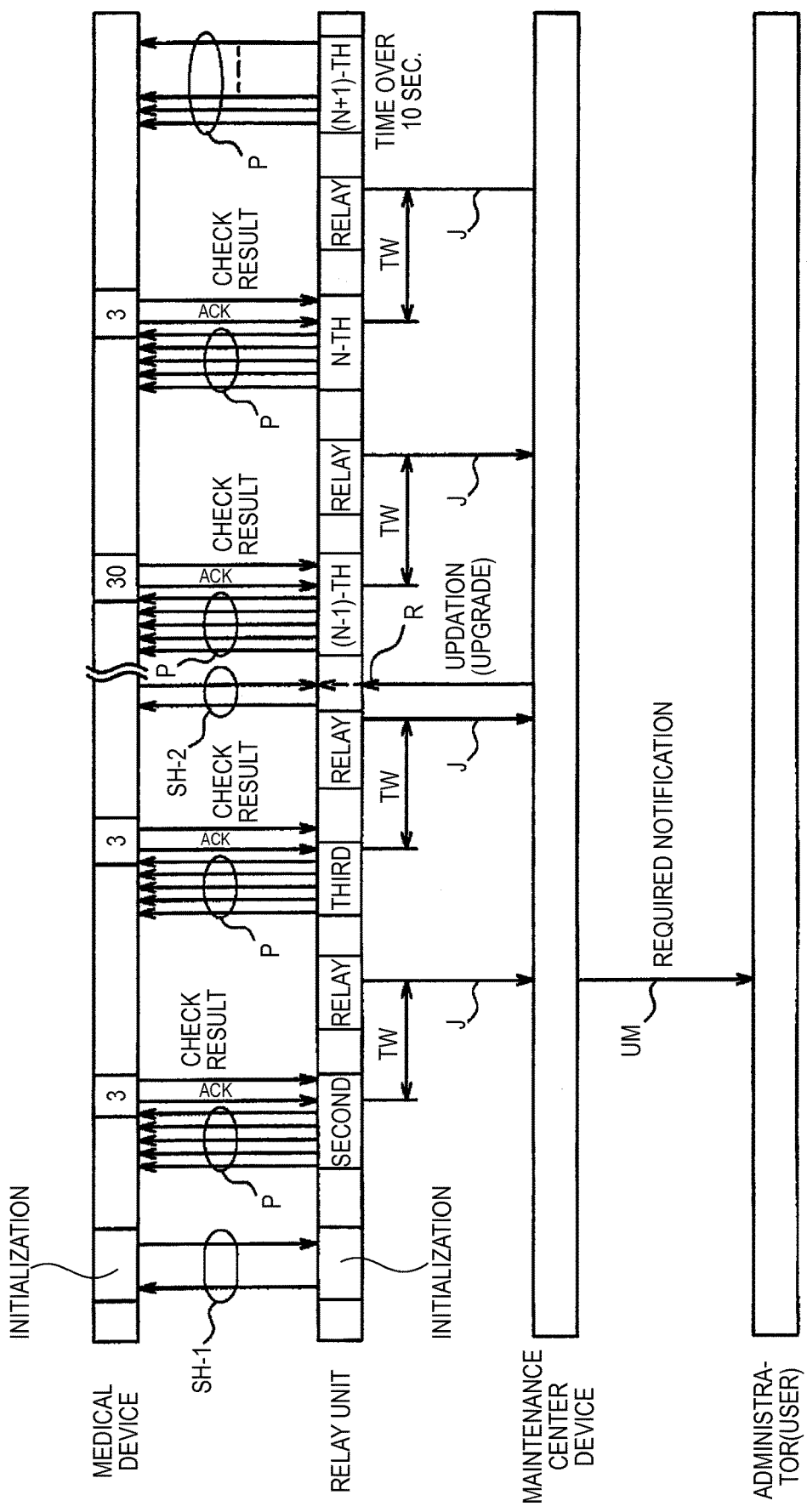
FIG. 9 is a time chart showing a remote maintenance operation in the embodiment of the remote maintenance system of the invention.

In the remote maintenance system of the invention, a time synchronizing process is performed on the medical device 10 and the relay unit 20. In initialization, as described above, the CPU 21 may receive the time information sent from the maintenance center device 30, and set the time information to the own timer to activate it. The time information which is sent from the relay unit 20 to the medical device 10 is the time information of the timer of the CPU 21 in the relay unit 20 at the transmission. The time information is input to the CPU 11, and the CPU sets the time of the own timer and starts the operation of the timer. Therefore, the times of the timers of the CPUs 21, 11 are synchronized with each other. In FIG. 9, this process is indicated as an initial synchronizing process SH1.

The numeral "3" shown in the time bar of the medical device (AED) 10 in FIG. 9 indicates a period of three seconds which is the time period of the checking process performed at a predetermined time of a day. In order to acquire a result of the daily check, the relay unit 20 performs polling P. After the initial synchronizing process SH1, the next polling P is set to be started a predetermined time period (for example, five seconds) earlier than elapse of 24 hours from a time of replying to the polling P. Alternatively, the CPU 21 of the relay unit 20 may perform the start control in the following manner. The polling start time and the time period which elapses before the medical device 10 replies to the polling P are stored in the memory, and, after the next of the initial synchronizing process SH1, the time when the polling P is next started is determined and stored while the time is advanced or retarded based on the difference of the time periods when, in each of the previous two pollings P, the power supply of the medical device 10 is turned ON automatically or by an external operation by the user and replies to the pollings. The time of starting the polling is substantially identical with that when the CPU 21 is changed from the sleep mode to the operation state, and this time is when a predetermined time period after, in the previous polling, the medical device 10 replies and the communication link is established. Alternatively, each time when the communication link is established, the time synchronizing process may be performed on the medical device 10 and the relay unit 20.

The numeral "30" shown in the time bar of the medical device (AED) 10 in FIG. 9 indicates a period of 30 seconds which is the time period of the checking process performed at a predetermined time of a month. In the monthly check, for example, the number of check items may be increased. In the case of the monthly check, the CPU 11 may transmit the present time, and the CPU 21 of the relay unit 20 may set the time of the own timer, thereby synchronizing the times.

In FIG. 9, the arrow R which is directed from the maintenance center device 30 to the relay unit 20 indicates an updation setting. In the case of the updation setting, the timer of the CPU 11 and that of the CPU 21 are synchronized with each other by an updation setting process SH2 which is similar to the above-described initial setting process.

In FIG. 9, the arrow J which is directed from the relay unit 20 to the maintenance center device 30 indicates relaying (transmission) of information based on the check result. As described above, the maintenance center device 30 receives information from a plurality of relay units 20. In the case where all medical devices are determined to be checked at the same time, therefore, there is a possibility that electronic mails from the relay units 20 may be transmitted at the same time and the processing load may exceed the processing capacity of the center device 30. In the initialization, as described above, the setting information therefore includes "the transmission waiting time period TW of information based on the check result". The terms "the transmission waiting time period TW of information based on the check result" mean the time period from the connection reply ACK of the medical device 10 to the timing when the relay unit 20 transmits information based on the check result to the maintenance center device 30. The time period depends on the processing capacity of the CPU 31, and is set differently for several tens of relay units, so that intervals of about 20 seconds are maintained among several tens of sets. According to the configuration, the CPU 31 can adequately process electronic mails which are transmitted from an enormous number of relay units 20.

At the (N+1)-th time in the time bar of the relay unit 20 in FIG. 9, a time-over detection in the communication is shown. In the case where the relay unit 20 is activated at a predetermined time and, even when polling to the medical device 10 is continued for 10 seconds or longer, there is no reply, the time over occurs, and the relay unit 20 transmits information indicative of abnormality due to a time over in the communication, as the determination result, to the maintenance center device 30 (the transmission is not shown). In this case, "the transmission waiting time period TW of information based on the check result" which elapses before transmission of abnormality may be counted from the detection of the time over.

In FIG. 9, the arrow UM which is directed from the maintenance center device 30 to the administrator (user) indicates transmission of an electronic mail from the maintenance center device 30 to the portable telephone or the like. Any one of the medical device 10, the relay unit 20, and the maintenance center device 30 performs determination of normality/abnormality by using the check result, and, if abnormality is detected, an electronic mail is sent to the corresponding administrator. Of course, the mail transmission standard of the database may be set so that, also in the case where the determination result indicates normality, an electronic mail is transmitted.

Figure 10:
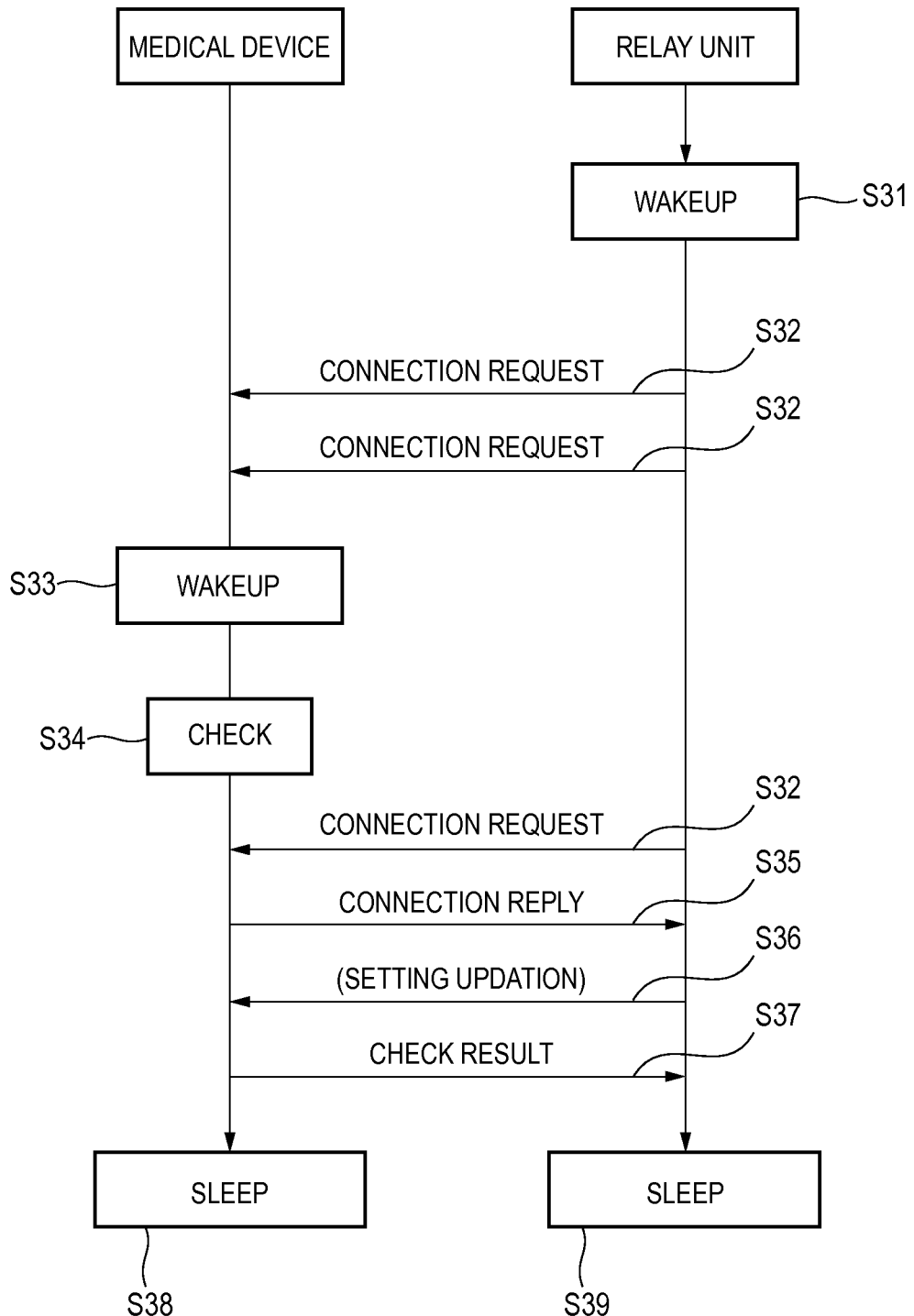
FIG. 10 is a sequence diagram showing a remote maintenance operation between the medical device and the relay unit in the embodiment of the remote maintenance system of the invention.

The usual operation of the thus configured remote maintenance system will be described with reference to the sequence diagram of FIG. 10. In the sleep mode, as described above, the CPU 21 of the relay unit 20 controls the power source portion so as to supply an electric power to various portions, at a predetermined time (for example, a predetermined time once a day, and at the same time as that in the medical device 10) based on the own timer, thereby causing the relay unit to enter the operation state (S31). Moreover, the CPU transmits (polling) the connection request command to the medical device 10 (S32).

In the sleep mode, as described above, the CPU 11 of the medical device 10 transfers to the operation state at a predetermined time in accordance with the own timer (S33). Although, in FIG. 10, the medical device 10 is lately operated, the medical device 10 possibly enters the operation state in an earlier timing because of an error of the timer. When entering the operation state, the CPU 11 controls the check processing portion 18 so as to check the states of the AED body portion 2, the power source portion 3, and the electrode pads 4, thereby obtaining a check result (S34). Also during this process, the polling is continued, and the communicating portion 16 of the medical device 10 transmits the connection reply command in response to the connection request command (S35). As a result, the communication link is established, and, as required, setting information related to updation is sent from the relay unit 20, so that the setting information is set in a similar manner as the above-described initial setting process (S36).

Furthermore, since the CPU 11 is obtained the check result in step S34, the CPU transmits information based on the check result through the communicating portion 16 (S37), controls the communicating portion 16 so as to disconnect the communication link, and transfers to the sleep mode (S38). After the CPU 21 of the relay unit 20 receives the information based on the check result through the communicating portion 23, the CPU controls the communicating portion so as to disconnect the communication link, and transfers to the sleep mode (S39).

Figure 11:
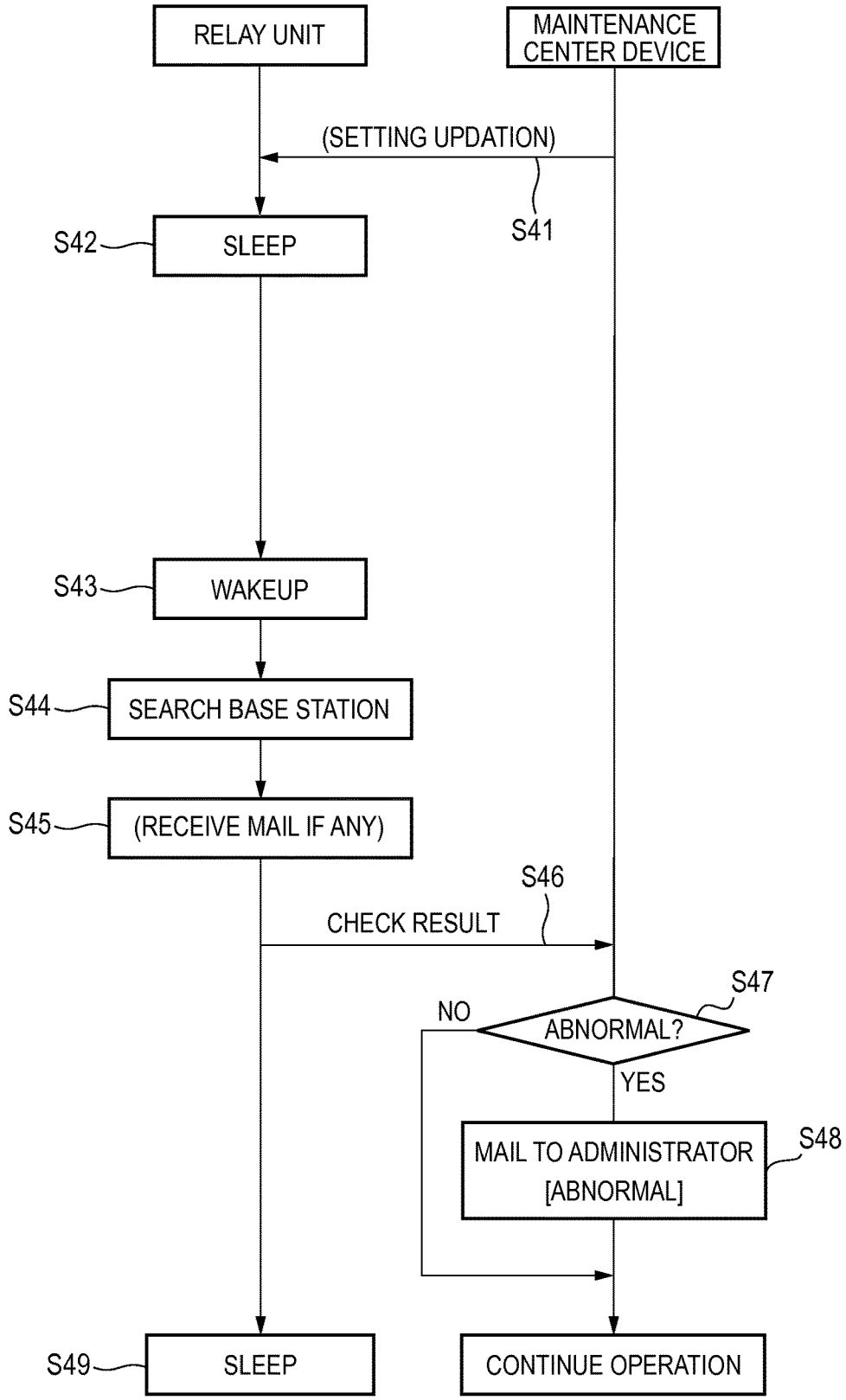
FIG. 11 is a sequence diagram showing a remote maintenance operation between the relay unit and the maintenance center device in the embodiment of the remote maintenance system of the invention.

Between the relay unit 20 and the maintenance center device 30, by contrast, a process is performed by the sequence shown in FIG. 11. If necessary, information related to updation is sent from the maintenance center device 30 to the relay unit 20, and the setting information is set in a similar manner as the above-described initial setting process (S41). Then, the CPU 21 of the relay unit 20 transfers to the sleep mode (S42). In the sleep mode, as described above, the CPU 21 of the relay unit 20 thereafter transfers to the operation mode in accordance with the own timer (S43). The time period from the transfer to the sleep mode in step S39 on FIG. 10 to step S43 is "the transmission waiting time period TW of information based on the check result".

In succession to step S43, by using the communicating portion 24, the CPU 21 searches the base station for transmitting an electronic mail (S44). When there is an incoming electronic mail, the mail is input to the CPU (S45). The CPU controls the check processing portion 29 to obtain a check result, transmits information based on the check result and that based on the check result sent from the medical device 10, to the maintenance center device 30 through the communicating portion 24 (S46), and transfers to the sleep mode (S49).

The CPU 31 of the maintenance center device 30 receives the information based on the check result through the communicating portion 33, reflects the information in the database of the memory 32, determines whether the information based on the check result is abnormal or not (S47), and, if abnormal, prepares a necessary electronic mail and transmits the electronic mail to the administrator through the communicating portion 34 (S48). The operation of the CPU is further continued.

In the embodiment, as described above, the relay unit 20 transfers from the sleep mode to the operation state in accordance with the check time of the medical device 10, collects information based on the check result from the medical device 10, performs a check on oneself, transmits information based on a result of the check to the maintenance center device 30, and then returns to the sleep mode. Therefore, the power consumption is very small, and remote maintenance can be performed for a long term by using a battery. Moreover, the relay unit is operated by a battery. Therefore, there is an advantage that a commercial power supply is not necessary to be disposed in the installation place, and the installation place is not limited.

In the embodiment, both the power source portion 3, which is the first power source, and the power source portion 27, which is the second power source, are configured by a battery. Alternatively, at least one of the power sources may be configured by a battery. Although, in the embodiment, the medical device 10 has been described as an AED, the invention can be applied to various medical devices such as a blood cell counter, an electrocardiogram, an electroencephalogram, and a bedside monitor.

In the case where the system of the invention is disposed (initial setting), check items may include a result of the operation check due to the user request on at least one of the medical device, the relay unit, the maintenance center device, and notification to the administrator. Specifically, in the case of the medical device, a check item of checking whether a function of the medical device normally operates or not, such as whether a checking unit can adequately acquire information of to-be-checked components or not, or whether the first communicator can adequately perform transmission to the relay unit or not may be included. Similarly, in the case of the relay unit, a check item of checking whether a function of the relay unit normally operates or not, such as whether the second communicator can adequately acquire information from the first communicator, or whether the third communicator can adequately perform transmission to the maintenance center or not may be included. Furthermore, in the case of the maintenance center device, a check item of checking whether a function of the maintenance center device normally operates or not, such as whether the fourth communicator can adequately acquire information from the third communicator, or whether the fifth communicator can adequately perform notification to the administrator or not may be included.

According to an aspect of the invention, the medical device includes the first power source controller which controls the ON/OFF operation of the first power source, and hence the power source can be turned ON during, for example, when a check by the checking unit is to be performed. Therefore, the power consumption can be reduced, so that the system can be placed in an environment where there is no commercial power supply. Moreover, the relay unit includes the second power source controller which automatically controls the ON/OFF operation of the second power source. Only when the relay unit communicates with the medical device and the maintenance center device, therefore the power source is requested to be turned ON. Therefore, the power consumption can be reduced, so that the relay unit can be placed in an environment where there is no commercial power supply. Remote maintenance can be applied also to a medical device which cannot be subjected to remote maintenance because of the installation place. When the activation time of the medical device is synchronized with that of the relay unit, particularly, remote maintenance can be realized with the minimum power consumption. Therefore, the system has an excellent feature that remote maintenance can be performed for a considerably long time period by power from a battery. Also when the system is used in a medical facility which has many medical devices, the relay unit can be placed in proximity to one of the medical devices, and hence a maintenance center can perform collective management without particularly considering the place where the medical device is installed.

According to an aspect of the invention, the relay unit can be placed in proximity to the medical device, and hence remote maintenance can be performed without depending on the size of the medical device itself. In the remote maintenance system of the invention, the maintenance center device transmits a message based on the information which is sent from the relay unit, to the administrator. In case of necessity, a necessary message is sent to the administrator, so that maintenance is performed on the medical device. Therefore, the problem can be known early and accurately, and preparation of members due to the problem, and the like can be promptly performed. Therefore, the problem can be quickly solved.

According to an aspect of the invention, any one of the medical device, the relay unit, and the maintenance center device includes the determiner which determines whether the check item is normal or abnormal, based on the check result. Therefore, determination of normality/abnormality can be performed in a desired device without human intervention. When, in this case, the result of the determination is notified to a predetermined administrator, maintenance can be performed on the medical device. This is convenient. When transmission to the administrator is allowed only when the result of the determination indicates abnormality, only a necessary message can be sent to the administrator.

According to an aspect of the invention, the medical device and the relay unit are separately disposed, and, when communication between the medical device and the relay unit is disabled, the result of the determination is set to indicate abnormality. In the case where information based on the check result cannot be collected because of a failure of the medical device or the like, therefore, the medical device can deal with the case as an abnormal state, and remote maintenance can be performed more safely and surely. Even when the relay unit conducts a process such as transmission to the maintenance center, the medical device is not affected by the process because the medical device is separately disposed. Therefore, an influence such as that the use of the medical device must be waited does not occur.

According to an aspect of the invention, after elapse of the predetermined time period, the relay unit transmits information received from the second communicator, to the maintenance center device through the third communicator. Even when there are many relay units, therefore, the transmission is dispersed, and hence the load of the maintenance center is reduced.

What is claimed is:
1. A remote maintenance system comprising:
an external medical device which includes:
a first power source;
a first power source controller which controls an ON/OFF operation of the first power source;
a checker which checks a check item; and
a first communicator which transmits first information including a result of a check by the checker, and
a relay unit which includes:
a second power source;
a second power source controller which automatically controls an ON/OFF operation of the second power source; and
a second communicator which communicates with the first communicator and which receives the first information from the first communicator,
wherein
after the first communicator transmits the first information to the second communicator, the first power source controller turns OFF the first power source,
in response to receiving of the first information by the second communicator, the second power source controller automatically turns OFF the second power source,
when the first power source is turned OFF, the first power source does not provide power to the checker, and
the checker checks the check item using a power, the power supplied from the first power source when the first power source controller turns ON the first power source.

2. The remote maintenance system according to claim 1, wherein
the relay unit includes a third communicator which communicates with a fourth communicator included in a maintenance center device, and
the third communicator transmits, to the fourth communicator, second information including the result of the check.

3. The remote maintenance system according to claim 2, wherein
the maintenance center device includes a fifth communicator which communicates with an administrator, and
the fifth communicator transmits, to the administrator, a notification based on the second information transmitted from the third communicator.

4. The remote maintenance system according to claim 2, wherein
the second power source controller automatically turns ON the second power source, at prescribed intervals or at a prescribed time, and
the second power source controller automatically turns OFF the second power source, after the second communicator of the relay unit receives the first information including the result of the check from the first communicator of the external medical device and the third communicator of the relay unit transmits the second information including the result of the check to the fourth communicator of the maintenance center device.

5. The remote maintenance system according to claim 2, wherein one of the external medical device, the relay unit and the maintenance center device includes a determiner which determines whether the check item is normal or abnormal based on the result of the check.

6. The remote maintenance system according to claim 5, wherein, when the determiner determines that the check item is abnormal, a fifth communicator of the maintenance center device transmits a notification to an administrator.

7. The remote maintenance system according to claim 5, wherein,
the check item includes communication between the external medical device and the relay unit, and
when the communication is disabled, the determiner determines that the communication is abnormal.

8. The remote maintenance system according to claim 2, wherein the maintenance center device changes and updates setting information of the relay unit and the external medical device, through the first to fourth communicators.

9. The remote maintenance system according to claim 2, wherein operation of at least one of the external medical device, the relay unit, the maintenance center device and a notification to an administrator check, which is requested by a user, is checked.

10. The remote maintenance system according to claim 2, wherein the second information transmitted from the third communicator of the relay unit to the fourth communicator of the maintenance center device includes information related to the relay unit.

11. The remote maintenance system according to claim 2, wherein, after elapse of a prescribed time period, the third communicator of the relay unit transmits the second information to the fourth communicator of the maintenance center device.

12. The remote maintenance system according to claim 2, wherein
the second power source controller automatically turns OFF the second power source, after the second communicator of the relay unit receives the first information including the result of the check from the first communicator of the external medical device and the third communicator of the relay unit transmits the second information including the result of the check to the fourth communicator of the maintenance center device.

13. The remote maintenance system according to claim 1, wherein
the first power source controller turns ON the first power source, at prescribed intervals or at a prescribed time.

14. The remote maintenance system according to claim 1, wherein the second power source controller turns ON the second power source before the first power source controller turns ON the first power source.

15. The remote maintenance system according to claim 1, wherein the check item includes at least one of a remaining amount of electric power of the first power source and an expiration period of an accessory of the external medical device.

16. The remote maintenance system according to claim 1, wherein the first information transmitted from the first communicator of the external medical device includes information for identifying the external medical device and information related to an installation place of the external medical device.

17. The remote maintenance system according to claim 1, wherein, when communication between the first communicator and the second communicator is established, the external medical device and the relay unit are synchronized in time with each other.

18. The remote maintenance system according to claim 1, wherein the second power source controller turns ON the second power source, after elapse of a prescribed time period from a timing when communication between the first communicator and the second communicator is established.

19. The remote maintenance system according to claim 1, wherein, after communication between the first communicator and the second communicator is established, the external medical device and the relay unit are synchronized in time with each other.

20. The remote maintenance system according to claim 1, wherein the first power source controller controls the ON/OFF operation of the first power source by an automatic operation or an external operation.

21. The remote maintenance system according to claim 1, wherein the external medical device is an AED.

22. The remote maintenance system according to claim 1, wherein the first power source and the second power source are identical with each other.

23. The remote maintenance system according to claim 1, wherein at least one of the first power source and the second power source is a battery.

24. The remote maintenance system according to claim 1, wherein communication between the first communicator and the second communicator is short-range wireless communication.

25. The remote maintenance system according to claim 1, wherein the first power source controller and the second power source controller are configured to automatically turn ON the first power source and the second power source, respectively, at the same time.

26. The remote maintenance system according to claim 1, wherein
the first communicator transmits the first information using the power supplied from the first power source when the first power source controller turns ON the first power source, and
the second communicator communicates with the first communicator using a power, the power supplied from the second power source when the second power source controller turns ON the second power source.

27. A remote maintenance system comprising:
an automated external defibrillator (AED) which includes:
a first battery;
a body portion;
electrode pads:
a first battery controller which controls an ON/OFF operation of the first battery:
a checker which checks, using a power supplied from the first battery when the first battery controller turns ON the first battery, a state of at least one of the first battery, the body portion, and the electrode pads; and
a first wireless communicator which transmits first information including a result of the check by the checker of the state of at least one of the first battery, the body portion, and the electrode pads,
wherein when the first battery is turned OFF, the first battery does not provide power to the checker; and
a relay unit comprising:
a second battery;
a second battery controller which turns ON/OFF the second battery at prescribed intervals or at a prescribed time;
a second wireless communicator which performs short-range wireless communication with the first wireless communicator; and
a communicator which transmits second information corresponding to the first information, which is transmitted from the first wireless communicator and is acquired from the second wireless communicator, wherein in response to receiving the first information from the first wireless communicator, the second battery controller automatically turns OFF the second battery, and the second wireless communicator communicates with the first wireless communicator using a power, the power supplied from the second battery when the second battery controller turns ON the battery.

28. The relay unit according to claim 27, wherein the remote maintenance system further includes a maintenance center device, and the communicator transmits the second information to the maintenance center device.

29. The relay unit according to claim 27, wherein the second battery controller is configured to automatically turn ON the second battery at the same time the first battery controller is programmed to automatically turn ON the first battery.

\* \* \* \* \*